United States Patent
Tsern et al.

(10) Patent No.: US 11,173,274 B2
(45) Date of Patent: Nov. 16, 2021

(54) SLEEPER DETECTION AND CONFIGURATION OF SLEEP ENVIRONMENTS AND LEARNING METHODS TO OPTIMIZE SLEEP QUALITY

(71) Applicants: Ely Tsern, Los Altos, CA (US); Jonathan Farringdon, Pittsburgh, PA (US); John Tompane, Los Altos, CA (US); Adam Hamel, Bradenton, FL (US); Mark Handel, Pittsburgh, PA (US)

(72) Inventors: Ely Tsern, Los Altos, CA (US); Jonathan Farringdon, Pittsburgh, PA (US); John Tompane, Los Altos, CA (US); Adam Hamel, Bradenton, FL (US); Mark Handel, Pittsburgh, PA (US)

(73) Assignee: Bryte, Inc., Los Altos, CA (US)

( * ) Notice: Subject to any disclaimer, the term of this patent is extended or adjusted under 35 U.S.C. 154(b) by 216 days.

(21) Appl. No.: 16/401,092

(22) Filed: May 1, 2019

(65) Prior Publication Data
US 2019/0336721 A1 Nov. 7, 2019

Related U.S. Application Data

(60) Provisional application No. 62/665,392, filed on May 1, 2018.

(51) Int. Cl.
*A61M 21/02* (2006.01)
*A61B 5/00* (2006.01)
*A61B 5/11* (2006.01)
*A61M 21/00* (2006.01)

(52) U.S. Cl.
CPC .............. *A61M 21/02* (2013.01); *A61B 5/11* (2013.01); *A61B 5/4815* (2013.01);
(Continued)

(58) Field of Classification Search
CPC ... A61B 5/0816; A61B 5/4812; A61B 5/6892; A61B 5/024; A61B 5/6891;
(Continued)

(56) References Cited

U.S. PATENT DOCUMENTS 7,524,279 B2 4/2009 Auphan
7,967,739 B2 6/2011 Auphan
(Continued)

FOREIGN PATENT DOCUMENTS

KR 10-2017-0065853 A 6/2017
WO WO 2018-023135 A1 2/2018

OTHER PUBLICATIONS

International Search Report on related PCT Application No. PCT/US2019/030291 from International Searching Authority (KIPO) dated Aug. 7, 2019.
(Continued)

*Primary Examiner* — Christine H Matthews
*Assistant Examiner* — Joshua Daryl D Lannu
(74) *Attorney, Agent, or Firm* — Klein, O'Neill & Singh, LLP

(57) ABSTRACT

A bed includes environmental control components, which may be temperature control components and pressure adjustment components in some embodiments. The environmental control components may be configured to provide different sleep environments based on identity of sleepers using or expected to use the bed. A controller may determine a number of sleepers for the bed, identify the sleepers, and determine if there is an expectation of later arrival of sleeper in determining a configuration for the environmental control components in providing a sleep environment for the bed.

6 Claims, 11 Drawing Sheets

(52) U.S. Cl.
CPC .......... *A61B 5/6892* (2013.01); *A61B 5/4812* (2013.01); *A61B 5/6891* (2013.01); *A61B 2562/0247* (2013.01); *A61M 2021/0066* (2013.01)

(58) Field of Classification Search
CPC .......... A61B 5/4815; A61B 2562/0247; A61B 5/1116; A61B 2560/0242; A61B 5/01; A61B 5/6805; A61B 5/11; A47C 31/008; A47C 21/048; A47C 27/061; A47C 23/047; A47C 31/123; A47C 27/083; A61M 2021/0066; A61M 2205/332; A61M 2230/62; A61M 2230/005; A61M 2205/84; A61M 2205/505; A61M 2205/3606; A61M 21/02
See application file for complete search history.

(56) References Cited

U.S. PATENT DOCUMENTS

| | | |
|---|---|---|
| 8,161,826 B1 | 4/2012 | Taylor |
| 8,533,879 B1 | 9/2013 | Taylor |
| 8,661,915 B2 | 3/2014 | Taylor |
| 8,690,751 B2 | 4/2014 | Auphan |
| 8,800,386 B2 | 8/2014 | Taylor |
| 9,642,470 B2 | 5/2017 | Taylor |
| 10,744,390 B1 | 8/2020 | Kahn et al. |
| 10,945,659 B1* | 3/2021 | Kahn .................. A61B 5/0205 |
| 2011/0010014 A1 | 1/2011 | Oexman et al. |
| 2013/0283530 A1* | 10/2013 | Main .................. A47C 27/083 5/600 |
| 2015/0351982 A1 | 12/2015 | Krenik |
| 2018/0042556 A1 | 2/2018 | Shahparnia et al. |

OTHER PUBLICATIONS

Written Opinion on related PCT Application No. PCT/US2019/030291 from International Searching Authority (KIPO) dated Aug. 7, 2019.

Extended European Search Report on related European Patent Application No. 19795858.0 from the European Patent Office (EPO) dated May 19, 2021.

* cited by examiner

311

313

| # | ID'ed | Expected | State |
|---|---|---|---|
| 0 | - | None | Do Nothing |
| 0 | - | [Use 1 sleeper values] | [Use 1 sleeper state] |
| 1 | 0 | None | Merge, default settings |
| 1 | 1 | None | Merge, profile |
| 1 | 0 | 2, No ID | Zones, default settings |
| 1 | 0 | 2, 2nd ID'ed | Zones, default and profile |
| 1 | 1 | 2, 2nd no ID | Zones, profile and default |
| 1 | 1 | 2, 2nd ID'ed | Zones, profile and profile |
| 2 | 0 | - | Zones, default settings |
| 2 | 1 | - | Zones, profile and default |
| 2 | 2 | - | Zones, profile and profile |

FIG. 5

SLEEPER DETECTION AND CONFIGURATION OF SLEEP ENVIRONMENTS AND LEARNING METHODS TO OPTIMIZE SLEEP QUALITY

CROSS REFERENCE TO RELATED APPLICATION

This application claims the benefit of the filing date of U.S. Provisional Patent Application No. 62/665,392, filed on May 1, 2018, the disclosure of which is incorporated by reference herein.

BACKGROUND OF THE INVENTION

The present invention relates generally to sleep environments, and more particularly to configuration of a potential multi-user sleep environment.

Sleep is generally a universal need for people. Sleep provides many physiological benefits, and a sound night's sleep is often desired by many. Unfortunately, some may not obtain a sound night's sleep, even when sufficient time and preparation for sleep is available.

Different people may desire different sleep settings for a sound night's sleep. Although most people may, within broad parameters, desire a similar sleep setting—e.g., being able to lie down in a reasonably temperate environment—different people may prefer a host of different environments at the detailed level. For example, different people may have different sleep postures, have slightly different circadian rhythms, or a host of other characteristics that imply that somewhat different sleep setting may be preferable for different people.

Arranging an appropriate sleep setting for a particular individual may be difficult, therefore. The difficulty may be compounded by beds that provide a sleep setting for multiple people simultaneously. Usage of such beds may vary based on when the users may go to bed, based on who those users are, and even if usage of the bed by multiple persons varies on a frequent or infrequent basis.

BRIEF SUMMARY OF THE INVENTION

Some aspects of some embodiments determine a number of sleepers in a bed; determines if the sleeper(s) in the bed may be identified; and conditions a sleep environment of the bed based on the number of sleepers and identities of the sleepers. Some embodiments further determine if there is an expectation that the number of sleepers in the bed is expected to change, and takes the expectation into account in conditioning the sleep environment of the bed. In some embodiments user sleep environment profiles for conditioning the sleep environment of the bed are available for identified sleepers, and such embodiments may utilize the user sleep environment profiles in conditioning the sleep environment of the bed. In some embodiments a default user sleep environment profile may be used in conditioning the sleep environment of the bed in the event of an unidentified sleeper.

Some aspects of some embodiments determine an identity of a sleeper on a bed by comparing information from sensors with information relating to users of the bed. In some embodiments the information from sensors comprises information from pressure sensors. In some embodiments the information from pressure sensors is information from an array of pressure sensors. In some embodiments the information from pressure sensors provides a pressure map. In some embodiments the information from pressure sensors provides an indication of weight of the sleeper. In some embodiments the information from pressure sensors provides an indication of a side of the bed the user entered and/or is upon. In some embodiments the information from sensors comprises information from biometric sensors. In some embodiments information regarding time of day at which the sleeper entered the bed is used, along with information relating to times of day the users have or are expected to enter the bed.

In some embodiments conditioning the sleep environment of the bed comprises controlling a temperature of a sleep surface of the bed and/or controlling firmness of the sleep surface of the bed.

Some embodiments provide a bed system, comprising: a sleep surface; sensors configured to sense sleepers on the sleep surface; components for conditioning a sleep environment of the sleep surface; and a controller configured to receive information from the sensors and to provide commands to the components for conditioning the sleep environment, the controller configured determine a number of sleepers on the sleep surface and to provide at least some different commands to the components based on at least a number of sleepers on the sleep surface.

In some embodiments the controller is further configured to determine identities of sleepers on the sleep surface based on information from the sensors and predetermined information regarding at least some of the sleepers. In some embodiments the sensors comprise pressure sensors. In some embodiments the pressure sensors provide information of a pressure map for the sleep surface to the controller. In some embodiments the pressure sensors provide an indication of weight of sleepers on the sleep surface to the controller. In some embodiments the controller is configured to ignore the indication of weight of a one of the sleepers if the weight is sufficiently below a predetermined weight. In some embodiments the pressure sensors provide information of a side of the sleep surface a sleeper enters. In some embodiments the predetermined information regarding at least some of the sleepers comprises information relating to times of day the sleepers are expected to enter the bed. In some embodiments the information relating to times of day the sleepers are expected to enter the bed comprises information of times of day the sleepers previously entered the bed. In some embodiments the predetermined information regarding at least some of the sleepers comprises, for each sleeper, at least one of a side of the sleep surface expected to be entered by the sleeper, a weight of the sleeper, an expected sleep posture of the sleeper, and a time of day the sleeper is expected to enter the bed. In some embodiments the components for conditioning the sleep environment of the sleep surface comprise components for controlling a temperature of the sleep surface and components for controlling firmness of the sleep surface. In some embodiments the controller is configured to provide commands to the components for conditioning the sleep environment of the sleep surface using sleeper environment profiles for each of the sleepers. In some embodiments the components for conditioning the sleep environment of the sleep surface comprise components for separately controlling a temperatures of a right side and a left side of the sleep surface and components for controlling separately controlling firmness of the right side and the left side of the sleep surface. In some embodiments the controller is further configured to determine a side of the sleep surface for each sleeper on the sleep surface. In some embodiments the controller is configured to provide commands to the components for conditioning the sleep environment of the sleep surface for each side of the sleep surface using the sleeper environment profiles for the sleeper on that side of the sleep surface. In some embodiments the sleeper environment profiles include a default profile for use with an unidentified sleeper. In some embodiments the controller is further configured to determine if there is an expected number and identities of sleepers on the sleep surface. In some embodiments the controller is configured to provide commands to the components for conditioning the sleep environment of the sleep surface for both sides of the sleep surface using a single sleep environment profile if the expected number of sleepers on the sleep surface is one sleeper. In some embodiments the controller is configured to utilize a double optimized sleeper environment profile if the pressure sensors indicate two people sleeping together. In some embodiments the controller is configured to determine an expected number of sleepers on the sleep surface based on information of historical use of the bed. In some embodiments the controller is configured to not condition the sleep environment if the expected number of sleepers is zero. In some embodiments the controller is configured to condition the bed for a sleeper prior to the sleeper entering the bed if the expected number of sleepers is non-zero. In some embodiments the controller is configured to condition the bed for an identified expected sleeper prior to the identified expected sleeper entering the bed using a sleep environment profile for the identified expected sleeper. In some embodiments the controller is configured to determine an expected number of sleepers on the sleep surface based on calendar information of a smartphone of a historical sleeper for the bed. In some embodiments the controller is configured to determine an expected number of sleepers on the sleep surface based on location information of a smartphone of a historical sleeper for the bed.

Some embodiments provide a method of conditioning a bed for sleeping, comprising: determining, by a controller, a number of sleepers in a bed; determining identities, by the controller, of the sleepers in the bed; and conditioning a sleep environment of the bed based on the number of sleepers and identities of the sleepers.

In some embodiments the bed provides a sleep surface for two sleepers, and temperature and firmness of the sleep surface for a right side of the sleep surface and a left side of the sleep surface are separately controllable. In some embodiments the sleep environment of the bed is conditioned based on a sleep environment profile associated with each of the sleepers. In some embodiments an identity of the sleeper may be an unknown sleeper, and a default sleep environment profile is associated with the unknown sleeper. Some embodiments further comprise determining whether there is an expectation that the number of sleepers in the bed will change, and conditioning both the right and left sides of the bed based on the sleep environment profile associated with a sleeper in the bed in response to determining that there is no expectation that the number of sleepers in the bed will change, and conditioning a side of the bed of the sleeper in the bed with the sleep environment profile associated with that sleeper and conditioning another side of the bed without the sleeper with the sleep environment profile associated with a sleeper expected to enter the bed. In some embodiments the controller determines a number of sleepers in the bed based on information from pressure sensors of the bed. In some embodiments the controller determines identities of the sleepers in the bed based on information from the pressure sensors in the bed. In some embodiments the controller utilizes historical usage of the bed in determining identities of the sleepers. In some embodiments the controller utilizes historical usage of the bed in determining whether there is an expectation that the number of sleepers in the bed will change. Some embodiments further comprise determining whether there is no expectation that the number of sleepers in the bed will change, and, in response to determining that there is no expectation that the number of the sleepers in the bed will change, conditioning both the right and left sides of the bed based on the sleep environment profile associated with a sleeper in the bed. In some embodiments the controller determines identities of sleepers in the bed based on information provided by a smartphone associated with a sleeper. In some embodiments the sleep environment of the bed is conditioned based on a sleep environment profile provided to the bed by a server. In some embodiments the sleep environment profile is associated with a sleeper, and the sleep environment profile is provided to the bed in response to a request from a smartphone associated with the sleeper. Some embodiments further comprise deleting the sleep environment profile provided to the bed in response to a request received from the smartphone associated with the sleeper.

These and other aspects of the invention are more fully comprehended upon review of this disclosure.

BRIEF DESCRIPTION OF THE FIGURES

FIG. 5 is a table showing mappings to sleep environment conditioning states in accordance with aspects of the invention.

DETAILED DESCRIPTION

Figure 1:
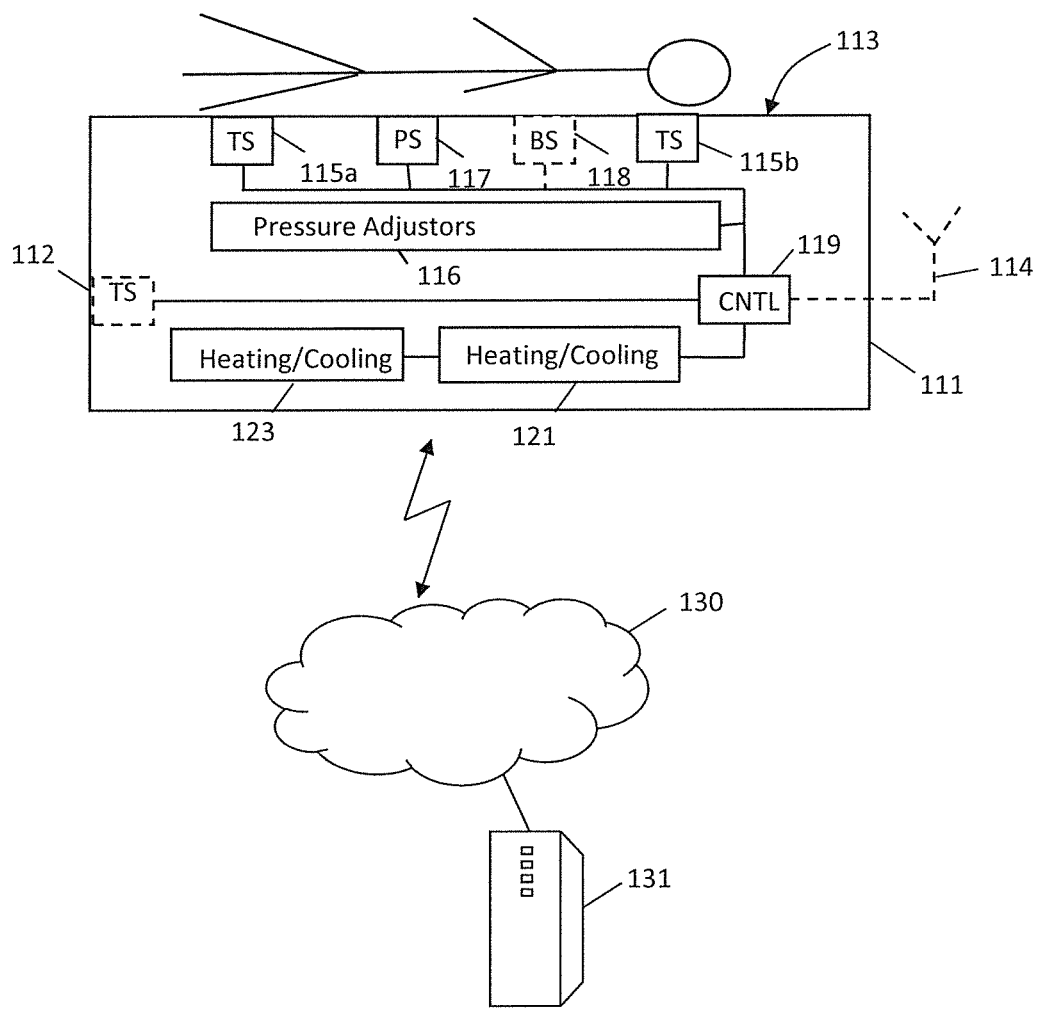
FIG. 1 is a semi-block diagram of a bed in accordance with aspects of the invention.

FIG. 1 is a semi-block diagram of a bed 111 in accordance with aspects of the invention. The bed of FIG. 1 includes a sleep surface 113 as an upper surface. In various embodiments, the sleep surface may be a top surface of a mattress, and in some embodiments the mattress, which itself may be comprised of multiple parts (separable or inseparable) may sit on top of a foundation, with the mattress and foundation considered the bed. In various embodiments, however, the bed may include other parts, and in some embodiments the various parts may be combined into one or more separable or non-separable items. The bed of FIG. 1 may be generally rectangular parallelepiped in form, although other forms may instead be used, and in various embodiments may house a variety of components and materials and be comprised of multiple separable components and/or layers. Generally a user, or multiple users depending on the bed, sleeps on the sleep surface.

The bed of FIG. 1 includes components for conditioning a sleep environment. For the example bed of FIG. 1, the components include a heating/cooling component 121 (and optional heating/cooling component 123) and a pressure adjustment component 116. The heating/cooling component allows for adjustment of temperature of the sleep surface of the bed. The pressure adjustment component allows for adjustment of firmness of the sleep surface.

The components for conditioning the sleep environment are generally commanded to do so by a controller 119. In generating commands, the controller may do so using information from sensors, for example temperature sensors 115a, b, pressure sensors 117, and, in some embodiments, biometric sensors 118. The controller also may make use of additional information, for example time-of-day information (for example maintained by the controller), information provided by users by way of user devices, and historical usage and/or sensor information maintained by the controller. In some embodiments the controller may command conditioning of the sleep environment as discussed in U.S. Provisional Patent Application No. 62/665,278, entitled SLEEP PHASE DEPENDENT TEMPERATURE CONTROL AND LEARNING METHODS TO OPTIMIZE SLEEP QUALITY, filed on even date herewith and/or U.S. Provisional Patent Application No. 62/665,283, entitled SLEEP PHASE DEPENDENT PRESSURE CONTROL AND LEARNING METHODS TO OPTIMIZE SLEEP QUALITY, filed on even date herewith, the disclosure of both of which are incorporated by reference for all purposes herein. As illustrated in FIG. 1, the controller is housed within the bed. In various embodiments the controller can be housed in either the mattress, base or be located externally outside of the bed. In some embodiments the controller comprises one or more processors. In some embodiments the controller is comprised of more than one processor, and the controller may be partitioned and housed in at least two separate physical enclosures, each with at least one processor. In some embodiments the controller is comprised of more than one processor, and the controller may be partitioned and housed in at least two separate physical enclosures, each with at least one processor. In some embodiments the controller is coupled to a network by way of wired or wireless communication circuitry, which may include for example antenna 114. In such embodiments the controller may be coupled (for example by a network 130 which may include the Internet) to a remote server 131, which in some embodiments may perform various of the functions ascribed to the controller herein.

The temperature sensors may be positioned in or adjacent the sleep surface, and provide an indication of a temperature of the sleep surface. In some embodiments, the temperature sensors are worn by the sleeper, provide an indication of a temperature of the sleeper's body or portion of body where the sensor is worn, and can be wired or wirelessly connected to the controller.

The pressure sensors may be located under the sleep surface, and provide an indication of pressure on the sleep surface. Alternatively, the pressure sensors may be located in the controller and connected via air tubes to air chambers underneath the sleep surface to measure the pressure in the air chambers. The biometric sensors may be located in or under the sleep surface, and may provide an indication of heart rate, breathing information, or other biometric information regarding the user on the sleep surface. In some embodiments the biometric sensors may be in an article worn by the user, for example a shirt, with the biometric sensors wirelessly communicating with the controller. In some embodiments the biometric sensors are as discussed or part of an item as discussed in J. Kelly et al., Recent Developments in Home Sleep-Monitoring Devices, ISRN Neurology, vol. 2012, article ID 768794, the disclosure of which is incorporated herein for all purposes.

In various embodiments the controller may condition the sleep environment in accordance with a configuration for the sleep environment determined by the controller. In some embodiments the controller determines the configuration for the sleep environment based on a number of sleepers in the bed, identification of the sleepers in the bed, and an expected later number and identification of sleepers in the bed.

In some embodiments the controller determines a number of sleepers in the bed based on information from the pressure sensors. In some embodiments motion sensors (not shown in FIG. 1) may provide information as to persons in the bed, and the controller may use information from the motion sensors in determining a number of sleepers in the bed.

In some embodiments the controller determines an identity or identities of sleeper(s) in the bed based on comparison of sensor information or other information with predetermined information of candidate sleepers. In some embodiments the controller compares information from the pressure sensors with predetermined information of candidate sleepers. For example, in some embodiments the controller estimates a weight of a person based on the information from the pressure sensors, and compares the estimate of the weight to weights of candidate sleepers, who may have previously provided the controller information regarding their weight. Also for example, in some embodiments the controller generates a pressure map, indicating locus of different pressure on the bed, and compares the pressure map with known pressure maps for candidate sleepers. In some embodiments the controller instead, or in addition, uses information from pressure sensors or motion sensors indicating a side of the bed from which a sleeper entered to identify the sleeper, or information from a microphone (not shown) associated with the bed, or presence of a smartphone in communication, for example via Bluetooth, WiFi or cellular communications, with the controller, or a time of entry into the bed. In some embodiments the controller can communicate and identify a different communication device for each sleeper and can use that identification information to determine which sleeper is close or closest to the bed. In some embodiments the controller with receives location and/or proximity information from the communication device of each sleeper, and uses this information to determine when each sleeper will enter the bed and when to start preparing the sleep environment for each sleeper to be ready when each sleeper enters the bed.

In some embodiments the controller determines an expected later number and identification of sleepers based on historical records for use of the bed. In some embodiments the controller instead or in addition uses calendar information, some of which may be stored in a smartphone or other device and communicated to the controller. For example, in some embodiments the controller maintains a record of indications that a second sleeper historically enters the bed at a certain time of day, which may vary based on the day of the week, or that the second sleeper historically enters the bed on certain days of the week. In such embodiments the controller may also maintain a record of identification of the second sleeper. In addition, in some embodiments the controller may also maintain, or receive, calendar based records of presence of the second sleeper, for example calendar records indicating that the second sleeper is in town or traveling out-of-town.

In some embodiments the heating/cooling component comprises a thermoelectric device, for example a Peltier device. In some embodiments the heating/cooling device comprises a heat pump. In some embodiments, the heating/cooling component may just be a heating component, for example a resistive heater, which in some embodiments may be adjacent or part of the sleep surface. In some embodiments, the heating/cooling component may just be a cooling component, for example an air conditioning device, which in some embodiments may be adjacent or part of the sleep surface. In some embodiments, the heating and/or cooling system includes combinations of heating and/or cooling devices. In the embodiment of FIG. 1 the heating/cooling component is illustrated within the bed, away from the sleep surface. In such embodiments, passageways allowing for thermal transfer between the heating/cooling component and the sleep surface may be provided. For example, in some embodiments, airway passageways are provided between the heating/cooling component and the sleep surface, and some embodiments include other components, for example one or more fans, to assist in conducting heat towards or away from the sleep surface. In some embodiments, where other fluids, for example liquids or fluids that may change between a gaseous and liquid state during use, may be used to control the temperature of the sleep surface, other fluid pathway structures, such as tubes, may be used to move fluids between the active heating and/or cooling component and the sleep surface. Collectively, in some embodiments the temperature control system can include heating and/or heating/cooling components and other fluid (including gaseous fluids) control components, such as fans. The bed may also include a second heating/cooling component 123. The use of a second heating/cooling component may be desirable, for example, in providing differentiation in temperature between different portions of the sleep surface, for example for different sides of the bed used by different users for sleep in a bed normally used by two people. In other embodiments vents or other devices or structures instead or in addition may be used to vary temperature across the sleep surface.

In some embodiments the pressure adjustment component comprises an array of controllable bladders or coils under the sleep surface of the bed. In some embodiments each of the coils is individually adjustable, so as to provide a different level of firmness to the surface of the bed.

Figure 2:
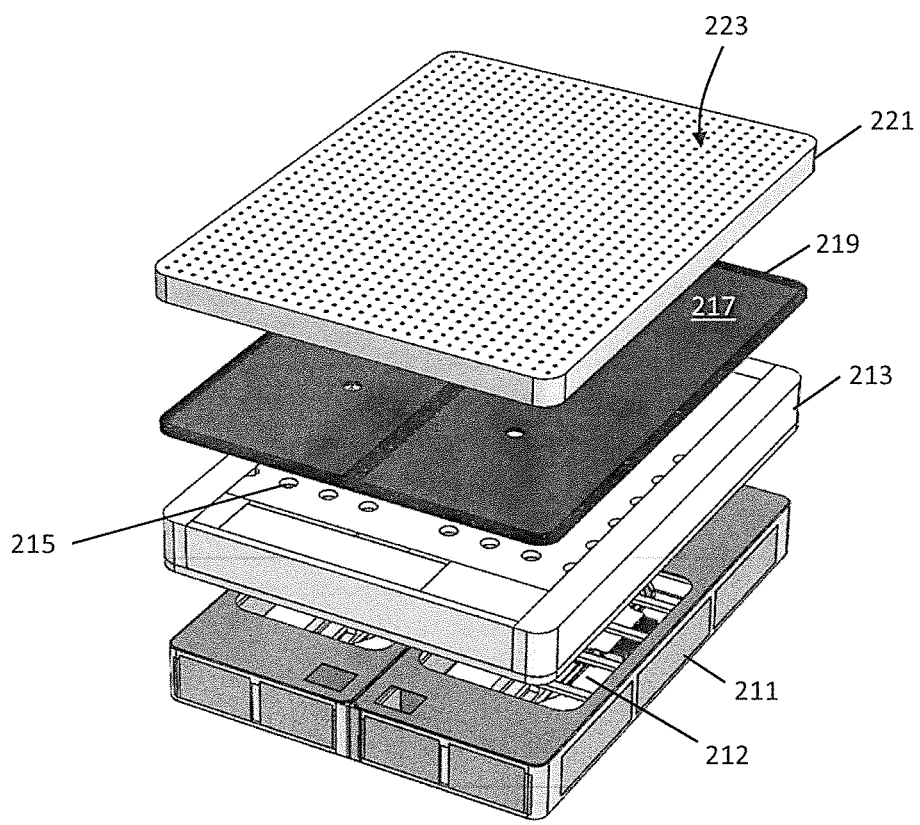
FIG. 2 is a diagrammatic expanded perspective view of a bed in accordance with aspects of the invention.

FIG. 2 is a diagrammatic exploded perspective view of a bed in accordance with aspects of the invention. The bed of FIG. 2 may be used as the bed of FIG. 1, in some embodiments.

The bed of FIG. 2 includes a substantially rectangular parallelepiped base 211. The base includes one or more apertures 212 in its upper surface, providing access to a generally open interior of the base. The interior of the base may include, for example, a heating/cooling component, and in some embodiments a controller for controlling the heating/cooling component and other controllable aspects of the bed (although in various embodiments the controller may be elsewhere located in, on, or about the structure of the bed). The apertures in the upper surface of the bed may provide for airflow from the heating/cooling component towards a sleep surface 223 of the bed. In many embodiments legs extend under corners or other portions of the base, for example to allow for the base to be raised off of the floor when in use. In such embodiments the base may also include apertures in a lower surface of the base, for example to provide for further airflow. The base may also include air pumps and associated items for a pressure adjustment component. In some embodiments, and as illustrated in FIG. 2, the base may in fact be two separate bases, positioned to abut one another in a side-by-side configuration.

A mattress of the bed is atop the base. The mattress is comprised of a core 213, with a reticulated foam layer 217 (bounded by a border 219) above the core and a foam pad 221 above the reticulated foam. The core, like the base, is of a generally rectangular parallelepiped form, with generally the same dimensions as the base. The core includes an array of inflatable bladders, which may generally cylindrical in form and considered coils, as part of the pressure adjustment component. The core also includes apertures extending through the core from an upper surface of the core to a lower surface of the core. The apertures allow for airflow from the base to the reticulated foam. The reticulated foam diffuses airflow from the core, such that air may diffusely reach the foam pad. Other embodiments may use other materials, such as other types of open structured fibers, that perform similar function of diffusing airflow.

The foam pad, in the embodiment of FIG. 2, also includes apertures through the pad, from an upper surface of the foam pad to a lower surface of the foam pad. The upper surface of the foam pad provides a sleep surface of the bed.

In operation, the heating/cooling component, under command of the controller, causes air of a desired temperature to exit the base and flow, through the core, reticulated foam, and pad, to the sleep surface. The pressure adjustment component, under command of the controller, individually adjusts pressure of the coils, and therefore adjusts firmness of different portions of the sleep surface.

Figure 3:
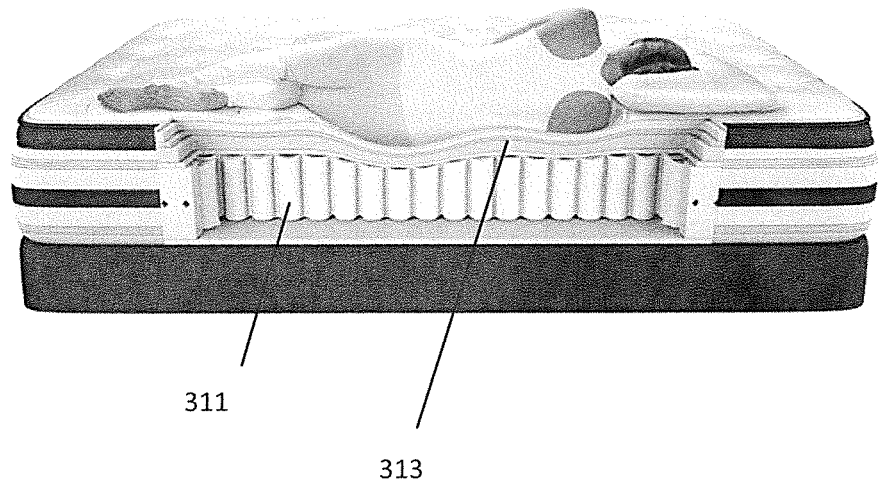
FIG. 3 is a semi-sectional side view of a bed in accordance with aspects of the invention, showing pressure adjustment coil cylinders for adjusting firmness of the sleep surface.

FIG. 3 is a semi-sectional side view of a bed in accordance with aspects of the invention, showing pressure adjustment coil cylinders for adjusting firmness of the sleep surface. The bed of FIG. 3 includes a sensor layer 313 just underneath a sleep surface of the bed. Adjustable coils 311, which may in the form of air bladders, are underneath the sensor layer, and provide adjustable support for a sleeper on the sleep surface.

Figure 4:
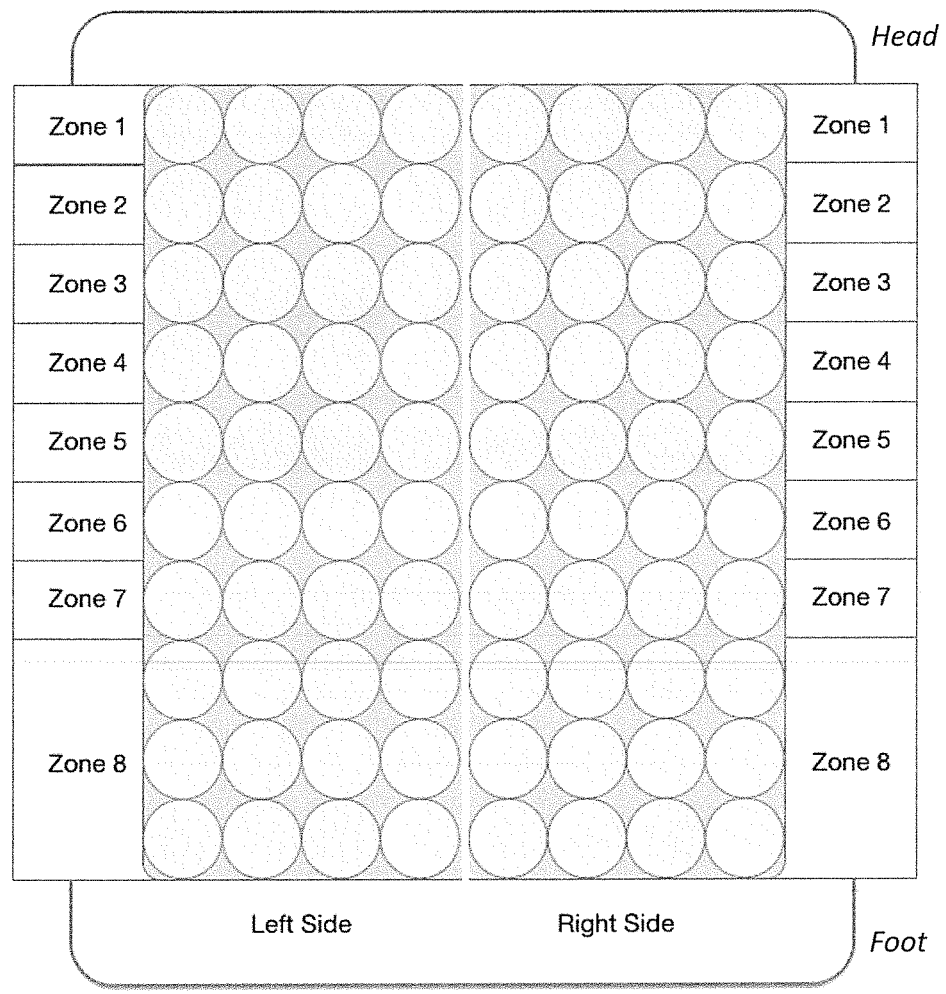
FIG. 4 is a semi-block diagram top view of pressure adjustment coil cylinders and indicating pressure sensor data locations of a bed in accordance with aspects of the invention.

FIG. 4 is a semi-block diagram top view of pressure adjustment coil cylinders and indicating pressure sensor data locations of a bed in accordance with aspects of the invention. The bed includes a left side and a right side. Generally each side is sized to accommodate a sleeper. The bed also includes what may be termed a head of the bed, stretching across a first end of the left and right sides, with a foot of the bed at a second end, opposite the first end. Sleepers will generally position their heads toward the head of the bed, with their feet towards the foot of the bed.

The bed includes an array of pressure adjustment coils or bladders. For the bed of FIG. 4, the array includes 80 bladders, arranged in a 10×8 array. In some embodiments each of the 80 bladders may be individually adjusted. For example, in some embodiments, pressure in each bladder or a group of bladders may be individually regulated, for example as commanded by the controller of FIG. 1.

In some embodiments a pressure fabric or mat or the like may be used to provide pressure indications to a controller. In some embodiments a pressure sensor is associated with each of the bladders. In such embodiments, the controller may receive an indication of pressure on the sleep surface about the location of each of the bladders. In some such embodiments the pressure sensor is positioned in the bed between the bladder and a sleep surface of the bed. In other of some such embodiments, the pressure sensor is associated with an air valve of a bladder or group of bladders.

In some embodiments a pressure sensor is associated with a plurality of bladders. For example, in the embodiment of FIG. 4, a first pressure sensor may be associated with a portion of a row of bladders closest to the head and on the left side of the bed, a second pressure sensor may be associated with a portion of the row of closest to the head and on the right side of the bed, and so on for each row of bladders. Alternatively, some (or all) of the pressure sensors may be associated with bladders of multiple rows. For example, in FIG. 4, a single pressure sensor may be provided for 16 zones, with eight zones on the left side of the bed and eight zones on the right side of the bed, each zone, other than zones closest to the foot of the bed, being for a single row of bladders, with the zones closest to the foot of the bed being for three rows of bladders.

In some embodiments the controller uses the information to determine one, some or all of a side of the bed entered by a sleeper, an estimation of weight of the user (for example based on a summation of pressure indications), a sleep position of the user (for example by a layout indicated by the pressure indications), and a number of sleepers (for example by pressure indications on both the left side and right side of the bed). In some embodiments the controller may also be configured to disregard some pressure indications, for example those for which a determined weight or layout indicates presence something other than a sleeper. For example, in some embodiments the controller may determine that the determined weight and/or layout indicates presence of a cat or dog on the bed, or one or more children on the bed (for example for cases in which the controller has not been provided information that a sleeper may be a child).

FIG. 5 is a table showing mappings to sleep environment conditioning states in accordance with aspects of the invention. The table includes a first column for number of sleepers in a bed, a second column for the number of the sleepers that are identified, a third column for a number of expected sleepers and whether the expected sleepers are identified, and fourth column for a state to which the bed should be configured. In some embodiments a controller, for example the controller of FIG. 1, determines information for the first three columns based on sensor information and historical and/or calendaring information, with the controller determining a row for selection of the state based on the first three columns.

The number of sleepers in the bed may be determined by the controller based on pressure sensor information, for example. The pressure sensor information may be used to determine whether a person (simply termed a sleeper) or more than one person is on the bed. Although some beds may accommodate more than two sleepers, for the purpose of discussion relating to FIG. 5, it will be assumed that the bed may accommodate up to two sleepers.

In some embodiments the controller identifies the sleeper(s) in the bed based on pre-configured information. For example, in some embodiments a sleeper may provide the controller with some or all of information as to a side of the bed to be entered by the sleeper, a weight of the sleeper, an expected sleep posture of the sleeper, a time of day the sleeper expects to enter the bed, or some other information. In some embodiments the sleeper may provide the controller such information by way of wireless communications from a smartphone device (for example to Bluetooth or Wi-Fi communication circuitry of or associated with the controller). In some embodiments the sleeper may provide the controller such information through an audio interface, for example a microphone, associated with the controller. In some embodiments the sleeper may provide the controller such information by way of a setup procedure for the bed. In some such embodiments the controller may also utilize information from pressure sensors and/or biometric sensors in identifying the sleeper. For example, the pressure sensors may indicate a side of the bed entered by the sleeper, the weight of the sleeper, and/or the sleep posture of the sleeper. Also for example, the biometric sensors may indicate a heart rate of the sleeper or other biological aspects of the sleeper, which also may be compared against information provided to the controller for use in identifying the sleeper.

In some embodiments the controller determines a number of expected sleepers and whether they are identifiable based on historical information or other information provided to the controller. For example, the controller may have been provided information that a second identified sleeper will be joining a first identified sleeper at a certain time of day every day. Alternatively, the controller may determine, for example based on pressure sensor information, that a second unidentified sleeper joins the first identified sleeper every other Tuesday.

Based on the number of sleepers, whether the sleepers are identified, and expected sleepers, the controller selects a state for configuring the bed. For example, if there is 1 sleeper, the sleeper is identified, and no later sleepers are expected, the controller may configure the bed to operate temperature controls for the both the left side and right side the same (e.g. merge the left zone and the right zone) and in accordance to a profile previously determined for the identified individual, and to operate the pressure controls for a single individual, again according to the profile for the identified individual. Alternatively, if there is 1 sleeper, the sleeper is identified, and an unidentified sleeper is expected to join the identified sleeper, the controller may configure the bed to operate the temperature controls and pressure controls for the zone occupied by the identified sleeper in accordance with the profile for that sleeper, and to operate the temperature controls and pressure controls for the other zone according to a default profile. Also for example, if there is 1 unidentified sleeper and some other entity that does not match a weight and/or layout of a sleeper, and no later sleepers are expected, the controller may configure the bed to operate temperature controls for the both the left side and right side the same (e.g. merge the left zone and the right zone) and in accordance to a default profile, and to operate the pressure controls for a single individual, again according to the default profile.

In various embodiments other states may in addition be used. In addition, in some embodiments selection of a state may utilize additional information, for example relative location of sleepers on the bed. The relative location of sleepers on the bed may be indicated, for example, by pressure sensors associated with the bed.

For example, when two sleepers move or start close to sleep together on the left or right side, the controller may, on the double occupied side, change the environment of the double occupied side to a configuration for which the bed environment modified for two people sleeping together, and may use a double occupied profile for doing so. For example, control of the temperature of the sleep surface may be commanded to a lower temperature in some embodiments, for example to account for increased warmth due to the proximity of the sleeper's bodies. In some such embodiments the controller may retain the prior configuration for the unoccupied side, for example in the event the unoccupied side is later re-occupied by the sleeper. Alternatively, in some embodiments the controller may merge both sides into one zone with the entire bed using a profile for couple-optimized configuration environment.

Also for example, when two sleepers move close to sleep together about a middle of the bed, in some embodiments the controller may merge both sides into one zone with the entire bed using the couple-optimized configuration environment. Alternatively, in some embodiments the controller may keep both sides the same as if both sleepers are completely on their side. Further, in some embodiments the controller may determine that two sleepers are in the bed with, for example, a child. In such embodiments the controller may configure environmental control of the bed to, for example merge environmental control of both sides of the bed into one zone, which in some embodiments may be controlled using a profile configuration for a combined couple and child.

Figure 6:
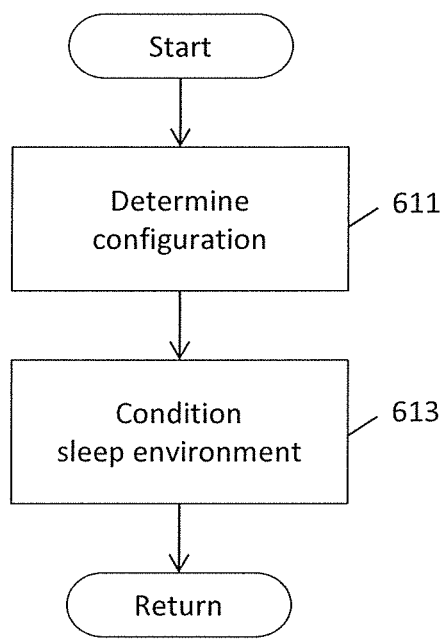
FIG. 6 is a flow diagram of a process for configuring a sleep environment in accordance with aspects of the invention.

FIG. 6 is a flow diagram of a process for configuring a sleep environment in accordance with aspects of the invention. In some embodiments the process is performed by a bed with a heating and/or cooling component and/or pressure adjustment component. In some embodiments the process is performed by a controller of a bed with a heating and/or cooling component and/or pressure adjustment component. In some embodiments the process is performed by a controller, which may be a processor, for example configured by program instructions.

In block 611 the process determines a configuration for control of a sleep environment of a bed. In some embodiments the configuration for control of the sleep environment is a configuration for control of temperature and/or pressure for a sleep surface of the bed. In some embodiments the bed includes multiple zones and the configuration for control of the sleep environment provides for merger of control of the multiple zones. In some embodiments the bed includes multiple zones and the configuration for control of the sleep environment provides for separate control of the multiple zones. In some embodiments the configuration for control of the sleep environment configures control of the sleep environment based on one or more sleeper sleep environment profiles. In some embodiments the process determines the configuration for control of the sleep environment based on a number of detected sleepers in the bed, and/or identification of the detected sleepers, and/or an expected number of and/or identification of later sleepers for the bed. In some embodiments the process ignores any entities on the bed for which weight, layout or other information indicates an entity which should not be considered a sleeper (e.g., a cat, a dog, or, in some embodiments, a child). In some embodiments the sleeper sleep environment profiles are profiles for the identified sleepers. In some embodiments the sleeper sleep environment profiles comprise a default profile. In some embodiments the default profile is used in the event a sleeper is not identified.

In block 613 the process conditions the sleep environment. In some embodiments the process commands a temperature for the configured zones of the sleep surface in accordance with one or more sleeper sleep environment profiles. In some embodiments the process commands a temperature for the configured zones of the sleep surface as discussed in U.S. Provisional Patent Application No. 62/665,278, entitled SLEEP PHASE DEPENDENT TEMPERATURE CONTROL AND LEARNING METHODS TO OPTIMIZE SLEEP QUALITY, and filed on even date herewith, the disclosure of which is incorporated by reference herein for all purposes. In some embodiments the process commands firmness for the configured zones of the sleep surface in accordance with one or more sleeper Sleep environment profiles. In some embodiments the process commands firmness for the configured zones of the sleep surface as discussed in U.S. Provisional Patent Application No. 62/665,283, entitled SLEEP PHASE DEPENDENT PRESSURE CONTROL AND LEARNING METHODS TO OPTIMIZE SLEEP QUALITY, and filed on even date herewith, the disclosure of which is incorporated by reference herein for all purposes.

The process thereafter returns.

Figure 7:
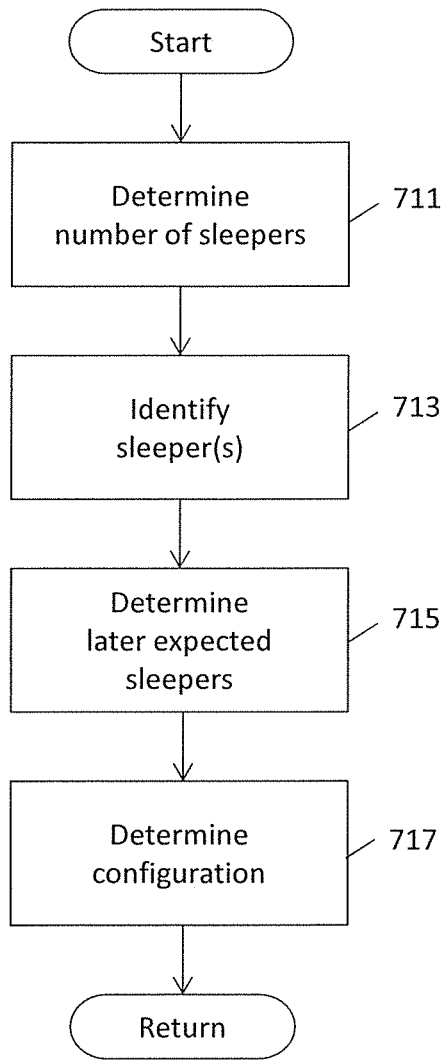
FIG. 7 is a flow diagram of a process for determining a configuration for a sleep environment in accordance with aspects of the invention.

FIG. 7 is a flow diagram of a process for determining a configuration for a sleep environment in accordance with aspects of the invention. In some embodiments the process is performed by a bed with a heating and/or cooling component and/or pressure adjustment component. In some embodiments the process is performed by a controller of a bed with a heating and/or cooling component and/or pressure adjustment component. In some embodiments the process is performed by a controller, which may be a processor, for example configured by program instructions. In some embodiments the process of FIG. 7 is used to perform operations of block 611 of the process of FIG. 6.

In block 711 the process determines a number of sleepers in the bed. In some embodiments the process determines the number of sleepers based on information from pressure sensors of the bed. In some embodiments the pressure sensors provide information of a pressure map for a sleep surface of the bed, and the process determines the number of sleepers based on information of the pressure map. For example in some embodiments sleepers may be expected to exert pressure over particular areas or particular lengths of the surface of the bed. Presence of such pressures may indicate a sleeper, while the lack of such presence of pressures, even if some pressures are indicated (by for example a cat), may indicate a lack of a sleeper. In some embodiments the pressure sensors provide information of an estimation of weight of sleepers in the bed, and the process determines the number of sleepers based on the estimation of weight of sleepers in the bed. In some such embodiments sleepers may be expected to be over a certain weight, and entities weighing less than the certain weight may not be considered sleepers. In some embodiments the pressure sensors provide information as to side(s) of the bed entered by sleepers, and the process determines the number of sleepers based on the number of sides of the bed used for entry by the sleepers.

In block 713 the process identifies sleepers in the bed. In some embodiments the process identifies a sleeper in the bed by comparing information from pressure sensors with information pertaining to one or more sleepers. In some embodiments the information pertaining to the sleeper(s) comprises one, some, or all of a side of the bed normally used for entry to the bed by the sleeper, a weight of the sleeper, and a sleep posture of the sleeper (such as side, back or front, or other postures in between those). In some embodiments the process in addition, or instead, uses an expected time of entry to the bed by the sleeper. In some embodiments the expected time of entry is based on historical records, for example maintained by the controller, of when the sleeper previously entered the bed. In some embodiments the expected time of entry is based on information provided by the user to the controller, for example provided by way of wireless communication between a smartphone of the user and wireless communication circuitry associated with the controller. In some embodiments the expected time of entry is based on location and proximity information provided by the user to the controller, for example provided by way of wireless communication between a smartphone of the user and wireless communication circuitry associated with the controller. In some embodiments the process identifies a sleeper in the bed by comparing information from biometric sensors with information pertaining to one or more sleepers. In some such embodiments, for example, the information pertaining to the sleepers may include a heart rate, a respiration rate, or other information. In some embodiments the process identifies a sleeper in the bed based on an audio input provided by the sleeper, and for example received by a microphone coupled to the controller.

In block 715 the process determines if later sleepers are expected, and the identities of the later sleepers, if determinable. In some embodiments the process determines if later sleepers are expected, and their identities if known, based on historical records of use of the bed, for example maintained by the controller. In some embodiments the process also uses calendar information for sleepers, for example provided to the controller by a smartphone, in determining if later identified sleepers are expected to use the bed.

In block 717 the process determines a configuration for sleep environment for the bed. In some embodiments, for example, the process uses the table of FIG. 5, or information of the table of FIG. 5, in determining a configuration for sleep environment for the bed.

Figure 8:
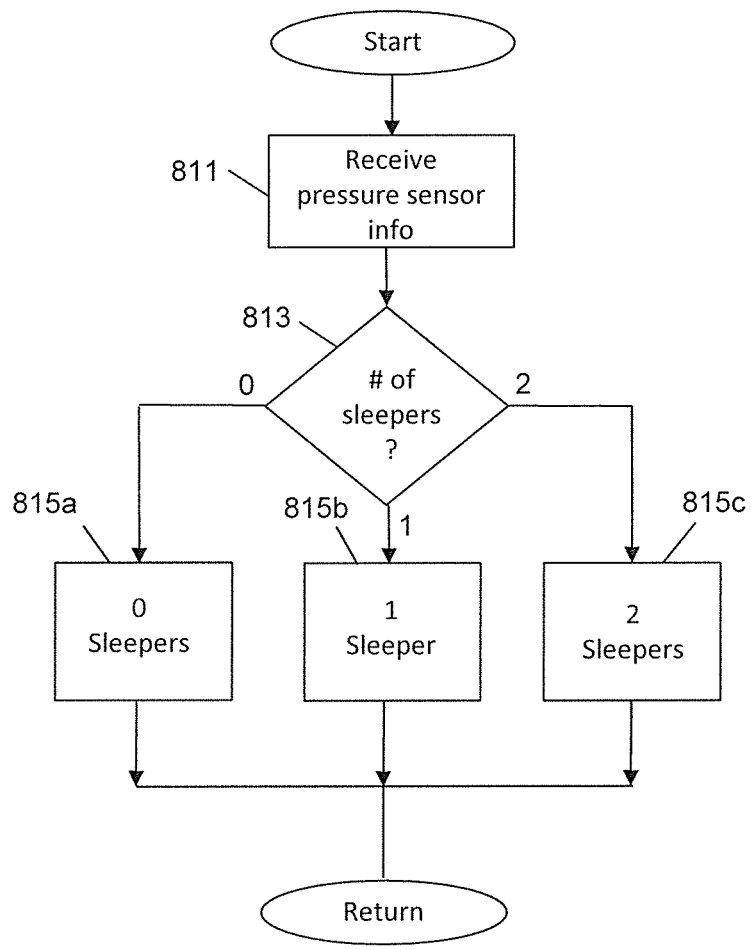
FIG. 8 is a flow diagram of a process for determining a number of sleepers in accordance with aspects of the invention.

FIG. 8 is a flow diagram of a process for determining a number of sleepers in accordance with aspects of the invention. In some embodiments the process is performed by a bed with a heating and/or cooling component and/or pressure adjustment component. In some embodiments the process is performed by a controller of a bed with a heating and/or cooling component and/or pressure adjustment component. In some embodiments the process is performed by a controller, which may be a processor, for example configured by program instructions. In some embodiments the process of FIG. 8 is used to perform operations of block 711 of the process of FIG. 7.

In block 811 the process receives information from pressure sensors of the bed. The pressure sensors indicate pressure applied to a sleep surface of the bed, for example due to weight of a sleeper being on the bed. In some embodiments the pressure sensors are part of a pressure fabric or mat. In some embodiments the pressure sensors are each associated with a coil or bladder of a pressure adjustment system. In some embodiments the pressure sensors are each associated with a plurality of coils or bladders of a pressure adjustment system.

In block 813 the process determines a number of sleepers on the bed. In some embodiments, and as shown in FIG. 8 for illustrative purposes, the number of sleepers on the bed may range from 0 to 2, inclusive. In some embodiments the process determines a number of sleepers based on information from the pressure sensors indicating a side of the bed from which a sleeper entered the bed; with for example information indicating the bed was not entered resulting in a determination of no sleepers, information indicating the bed was entered from one side by a sleeper resulting in a determination of one sleeper, and information indicating the bed was entered from two sides resulting in a determination of two sleepers. In some embodiments the process determines a number of sleepers based on information from pressure sensors indicating a sleeper on halves of the bed, for example a left half of the bed and a right half of the bed. In such embodiments, information indicating no sleepers results in a determination of no sleepers, information indicating a sleeper on only one half of the bed results in a determination of one sleeper, and information indicating a sleeper on both halves of the bed results in a determination of two sleepers.

For a determination of no sleepers, the process sets a memory location indicating no sleepers in block 815*a*. For a determination of one sleeper, the process sets a memory location indicating one sleeper in block 815*b*. For a determination of two sleepers, the process sets a memory location indicating two sleepers in block 815*c*.

The process thereafter returns.

Figure 9:
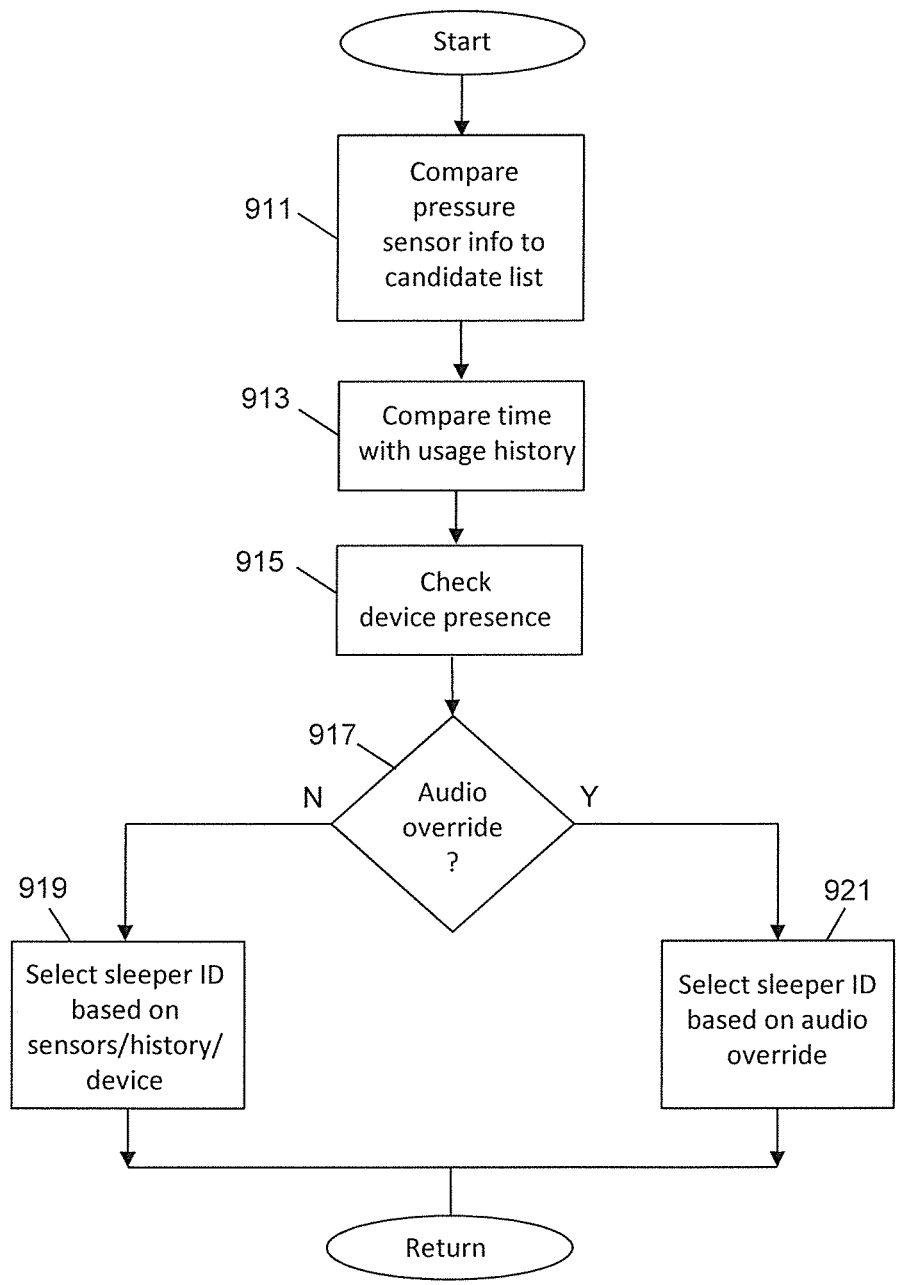
FIG. 9 is a flow diagram of a process for identifying sleepers in accordance with aspects of the invention.

FIG. 9 is a flow diagram of a process for identifying sleepers in accordance with aspects of the invention. In some embodiments the process is performed by a bed with a heating and/or cooling component and/or pressure adjustment component. In some embodiments the process is performed by a controller of a bed with a heating and/or cooling component and/or pressure adjustment component. In some embodiments the process is performed by a controller, which may be a processor, for example configured by program instructions. In some embodiments the process of FIG. 9 is used to perform operations of block 713 of the process of FIG. 7.

In block 911 the process compares information from pressure sensors with expected information for possible candidate sleepers. In some embodiments the information from pressure sensors indicates a half of the bed being slept on by a sleeper, with the half of the bed being either the left half of the bed or the right half of the bed in some embodiments. In such embodiments, the controller, for example, may maintain information as to which half of the bed a particular sleeper sleeps on. In some embodiments each of two sleepers has configured the bed to assign one unique side of the bed to each sleeper, and that configuration information of bed side assignments is stored in the controller and used for determining which sleeper is in the bed for future sessions. In some embodiments the information from the pressure sensors indicates a sleep posture of the sleeper, and the information for possible candidate sleepers includes information as to expected sleep postures of the candidate sleepers.

In block 913 the process compares time of entry to the bed with usage history of the bed by candidate sleepers. For example, in some embodiments the controller maintains a record of time of usage, or a record of time of entry to the bed, by particular sleepers.

In block 915 the process checks for presence of communication devices associated with particular sleepers. In some embodiments, the controller has associated wireless communication circuitry, for example Bluetooth or Wi-Fi communication circuitry, and the controller determines if communication with a device associated with particular sleepers is available. In some embodiments the controller can communicate and identify a different communication device for each sleeper and can use that identification information to determine which sleeper is close or closest to the bed. In some embodiments the controller with receives location and/or proximity information from the communication device of each sleeper, and uses this information to determine when each sleeper will enter the bed and when to start preparing the sleep environment for each sleeper to be ready when each sleeper enters the bed. In some embodiments, the criteria to decide whether a sleeper will be expected to sleep in the bed for that night is determined by a predetermined distance between the sleeper's location from their communications device and the bed location at a given time and the amount of remaining time before a scheduled sleep time. In some embodiments, if one sleeper is not expected to sleep in the bed that night based on this criteria, the bed will configure both sides of the bed to the personal configuration of the second sleeper. In some embodiments, if both sleepers are not expected to sleep in the bed that night based on this criteria, the bed will configure both sides of the bed to be turned off for that sleep session.

In block 917 the process determines if an audio input, for example to a microphone associated with the bed, has been received, with the audio input identifying a sleeper. If the audio input has been received, the process goes to block 921, and identifies the sleeper based on the audio input, and thereafter returns. Otherwise the process continues to block 919.

In block 919 the process identifies the sleeper based on the pressure sensor information, the usage history, and device presence, or based on one or some of those. For example, in some embodiments, the comparison of the pressure sensor information with expected information for candidate sleepers may indicate the sleeper is a particular identifiable individual. In some embodiments, the particular identifiable individual may be determined to be the sleeper. In some embodiments the comparison may indicate that the sleeper may be one of several candidate sleepers. In such embodiments, the process may narrow down the candidate sleepers to a particular identifiable sleeper based on, for example, time of entry to the bed and usage history and/or device presence. In some embodiments the process identifies the sleeper as an unidentified sleeper, for example if the process is not able to identify the sleeper as a particular identifiable sleeper.

The process thereafter returns.

Figure 10:
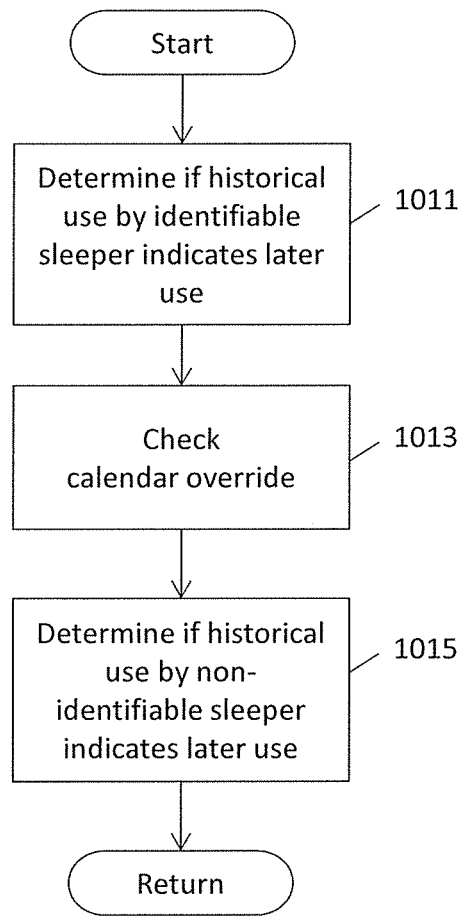
FIG. 10 is a flow diagram of a process for determining an expectation of later sleeper use in accordance with aspects of the invention.

FIG. 10 is a flow diagram of a process for determining an expectation of later sleeper use in accordance with aspects of the invention. In some embodiments the process is performed by a bed with a heating and/or cooling component and/or pressure adjustment component. In some embodiments the process is performed by a controller of a bed with a heating and/or cooling component and/or pressure adjustment component. In some embodiments the process is performed by a controller, which may be a processor, for example configured by program instructions. In some embodiments the process of FIG. 10 is used to perform operations of block 715 of the process of FIG. 7.

In block 1015 the process determines if historical use by an identifiable sleeper indicates later use of the bed. In some embodiments the controller maintains a record of time of entry to the bed by identified sleepers, and the process uses this information to determine if the identifiable sleeper is expected to enter the bed at a later time.

In block 1017 the process determines if historical use by the identifiable sleeper should be ignored based on information from a calendar for the identifiable sleeper. For example, the calendar for the identifiable sleeper may indicate the identifiable sleeper is out of town, with the implication that the identifiable sleeper will not be entering the bed. For example, the GPS location information of the communication of the identifiable sleeper may indicate the identifiable sleeper is out of town, with the implication that the identifiable sleeper will not be entering the bed.

In block 1015 the process determines if historical use by a non-identifiable sleeper indicates later use. For example, the controller may maintain records of entry to the bed of an unidentified sleeper, and, such records may indicate, for example, that the unidentified sleeper enters the bed later every Tuesday. In such a circumstance, every Tuesday the controller may determine that an unidentified sleeper is expected to later enter the bed.

The process thereafter returns.

Figure 11:
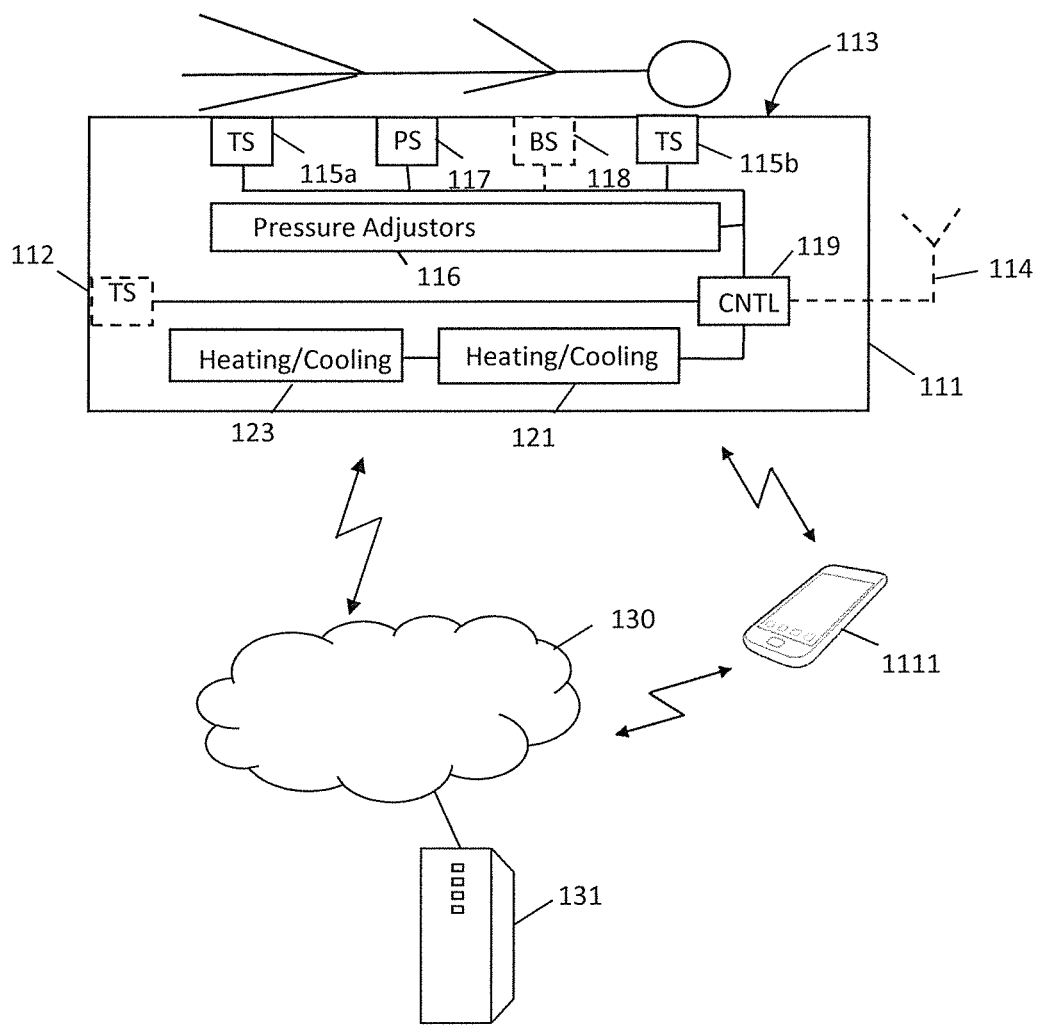
FIG. 11 is a semi-block diagram of a bed in a networked environment in accordance with aspects of the invention.

FIG. 11 is a semi-block diagram of a bed in a networked environment in accordance with aspects of the invention. The bed may be the bed of FIG. 1 in various embodiments, and as illustrated in FIG. 11 the bed generally includes the various items of the bed of FIG. 1. Accordingly, except as possibly discussed below, reference may be had to the discussion of FIG. 1 for items of the bed.

As discussed with respect to FIG. 1, the controller 119 of the bed of FIG. 11 is coupled to a network by way of wired or wireless communication circuitry, which may include for example antenna 114. In such embodiments the controller may be coupled (for example by a network 130 which may include the Internet) to a remote server 131. As further illustrated in FIG. 11, the controller may also communicate with a smartphone 1111, either directly, for example using Bluetooth communications, through a local network device (not shown in FIG. 11), or through the remote server.

In some embodiments the smartphone stores information of a sleeper sleep environment profiles for a user associated with the smartphone. The sleeper sleep environment profiles may include information which may be used by the controller in determining commanded sleep surface temperatures and commanded sleep surface firmness for the bed. In such embodiments, the smartphone may provide the sleeper sleep environment profiles to the bed, for use in conditioning a sleep environment for the user. The user may therefore, through use of the user's smartphone, be able to configure a bed, such as the bed of FIGS. 1 and 11, for use by the user.

In some embodiments the smartphone may transmit a request for available configurable beds, with the bed responding to the request, such that the smartphone and bed may thereafter communicate. In some embodiments bed network identification information may be attached to or printed on material on or near the bed, the information being for example an alphanumeric code or QR code or the like. In such embodiments the smartphone may be able to make use of the bed network identification information in arranging communications with the controller of the bed. In some embodiments a password may also be attached to or printed on material on or near the bed, or otherwise made available to the user, for use in arranging communications with the bed. Such may be useful, for example, in avoiding undesired access to the bed.

In some embodiments the remote server may store information of the sleeper sleep environment profiles for the user. In such embodiments the user may, through use of the smartphone or other network device, provide the remote server information to identify the bed, and in some embodiments, to allow the remote server to provide information of the sleeper sleep environment profiles to the bed. Accordingly, in some embodiments the remote server may provide information of the sleeper sleep environment to the bed. In some embodiments the bed may provide the smartphone bed identification information, which the smartphone may provide to the remote server. In various embodiments, the smartphone may also provide user identification information to the remote server, along with, in some embodiments, a password or key or the like for use in validating the user ID, or that use of the user ID is an authorized use.

In some embodiments the smartphone may also provide information as to which side of the bed the user will use, and/or whether the user will be the only sleeper in the bed. In some embodiment the user may also be allowed to provide information regarding a second sleeper in the bed, including in some embodiments information of sleeper sleep environment profiles for the second sleeper (if so authorized, for example by way of having authentication permission from the second sleeper). In some embodiments the controller, or the remote server, may request such information from the smartphone, or provide an interface for the smartphone to provide such information.

In some embodiments the smartphone may also provide a request to delete information regarding the user from the bed. In some embodiments the controller may also be configured to delete the information regarding the user after an expected wake time of the user, or at or after the expected wake time and the user is no longer on the bed.

Although the invention has been discussed with respect to various embodiments, it should be recognized that the invention comprises the novel and non-obvious claims supported by this disclosure.

What is claimed is:

1. A bed system, comprising:
    a sleep surface;
    sensors configured to sense sleepers on the sleep surface;
    components for conditioning a sleep environment of the sleep surface; and
    a controller configured to receive information from the sensors and to provide commands to the components for conditioning the sleep environment, the controller configured to determine a number of sleepers on the sleep surface and to provide at least some different commands to the components based on at least the number of sleepers on the sleep surface;
    wherein the controller is further configured to determine identities of sleepers on the sleep surface based on information from the sensors and predetermined information regarding at least some of the sleepers;
    wherein the controller is further configured to determine if there is an expected number and expected identities of sleepers on the sleep surface; and
    wherein the controller is configured to determine the expected number of sleepers on the sleep surface based on location information of a smartphone of a historical sleeper for the bed system.

2. A method of conditioning a bed for sleeping, comprising:
    determining, by a controller, a number of sleepers in a bed;
    determining identities, by the controller, of the sleepers in the bed; and
    conditioning a sleep environment of the bed based on the number of sleepers and the identities of the sleepers;
    wherein the bed provides a sleep surface for two sleepers, and temperature and firmness of the sleep surface for a right side of the sleep surface and a left side of the sleep surface are separately controllable; and
    wherein the sleep environment of the bed is conditioned based on a sleep environment profile associated with each of the sleepers; and
    further comprising determining whether there is an expectation that the number of sleepers in the bed will change, and conditioning both the right and left sides of the bed based on the sleep environment profile associated with a sleeper in the bed in response to determining that there is no expectation that the number of sleepers in the bed will change, and conditioning a side of the bed of the sleeper in the bed with the sleep environment profile associated with that sleeper and conditioning another side of the bed without the sleeper with the sleep environment profile associated with a sleeper expected to enter the bed.

3. The method of claim 2, wherein the controller determines the identities of the sleepers in the bed based on information from pressure sensors in the bed.

4. The method of claim 3, wherein the controller utilizes historical usage of the bed in determining the identities of the sleepers.

5. The method of claim 3, wherein the controller utilizes historical usage of the bed in determining whether there is an expectation that the number of sleepers in the bed will change.

6. The method of claim 2, further comprising determining whether there is no expectation that the number of sleepers in the bed will change, and, in response to determining that there is no expectation that the number of the sleepers in the bed will change, conditioning both the right and left sides of the bed based on the sleep environment profile associated with a sleeper in the bed.

* * * * *